US00PP23105P2

(12) United States Plant Patent
Ren

(10) Patent No.: US PP23,105 P2
(45) Date of Patent: Oct. 9, 2012

(54) ***ECHINACEA* PLANT NAMED 'BALSOMSED'**

(50) Latin Name: *Echinacea×hybrida*
Varietal Denomination: Balsomsed

(75) Inventor: Jianping Ren, Geneva, IL (US)

(73) Assignee: Ball Horticultural Company, West Chicago, IL (US)

( * ) Notice: Subject to any disclaimer, the term of this patent is extended or adjusted under 35 U.S.C. 154(b) by 0 days.

(21) Appl. No.: 13/136,312

(22) Filed: Jul. 27, 2011

(51) Int. Cl.
*A01H 5/00* (2006.01)

(52) U.S. Cl. ..... Plt./428

(58) Field of Classification Search ..... Plt./428
See application file for complete search history.

*Primary Examiner* — Kent L Bell
(74) *Attorney, Agent, or Firm* — Audrey Charles

(57) ABSTRACT

A new and distinct cultivar of *Echinacea* plant named 'Balsomsed', characterized by its single-type, deep red-orange colored inflorescences, medium green-colored foliage, and moderately vigorous, compact-upright growth habit, is disclosed.

1 Drawing Sheet

Latin name of genus and species of plant claimed: *Echinacea×hybrida.*

Variety denomination: 'Balsomsed'.

BACKGROUND OF THE INVENTION

The present invention relates to a new and distinct cultivar of *Echinacea* plant botanically known as *Echinacea×hybrida* and hereinafter referred to by the cultivar name 'Balsomsed'.

The new cultivar originated in a controlled breeding program in Elburn, Ill. during September 2007. The objective of the breeding program was the development of *Echinacea* cultivars with a single inflorescence form having imbricate ray florets and a well-branched, compact growth habit.

The new *Echinacea×hybrida* cultivar is the result of cross-pollination. The female (seed) parent of the new cultivar is the proprietary *Echinacea×hybrida* breeding selection designated 'E33-5', U.S. Pat. No. 7,982,110, characterized by its single-type, red-orange colored flowers, medium green-colored foliage, and moderately vigorous, upright growth habit. The male (pollen) parent of the new cultivar is from a bulk pollen mix of seven proprietary *Echinacea×hybrida* breeding selections designated 'E33-1' through 'E33-7', U.S. Pat. No. 7,982,110, characterized by their single-type, shades of red-orange colored inflorescences, medium green-colored foliage, and moderately vigorous, upright growth habit. The new cultivar was discovered and selected as a single flowering plant within the progeny of the above stated cross-pollination during October 2008 in a controlled environment in Elburn, Ill.

Asexual reproduction of the new cultivar by in vitro propagation since October 2008 in West Chicago, Ill. has demonstrated that the new cultivar reproduces true to type with all of the characteristics, as herein described, firmly fixed and retained through successive generations of such asexual propagation.

SUMMARY OF THE INVENTION

The following characteristics of the new cultivar have been repeatedly observed and can be used to distinguish 'Balsomsed' as a new and distinct cultivar of *Echinacea* plant:

1. Single-type, deep red-orange colored inflorescences;
2. Medium green-colored foliage; and
3. Moderately vigorous, compact-upright growth habit.

Plants of the new cultivar differ from plants of the female and male parents primarily in inflorescence color and growth habit. The new variety is more compact and has a different red-orange inflorescence color shade than the parent plants.

Of the many commercially available *Echinacea* cultivars, the most similar in comparison to the new cultivar is *Echinacea* 'Tomato Soup', U.S. Plant Pat. No. 19,427. However, in comparison, plants of the new cultivar differ from plants of 'Tomato Soup' in at least the following characteristics:

1. Plants of the new cultivar have shorter ray florets than plants of 'Tomato Soup'; and
2. Plants of the new cultivar are more compact, as measured by plant height, than plants of 'Tomato Soup'.

BRIEF DESCRIPTION OF THE PHOTOGRAPHS

The accompanying photographs show, as nearly true as it is reasonably possible to make the same in color illustrations of this type, typical inflorescence and foliage characteristics of the new cultivar. Colors in the photographs differ slightly from the color values cited in the detailed description, which accurately describes the colors of 'Balsomsed'. One plant per 1 gallon container was grown for 16 weeks in a greenhouse in Elburn, Ill.

DETAILED BOTANICAL DESCRIPTION

Figure 1:
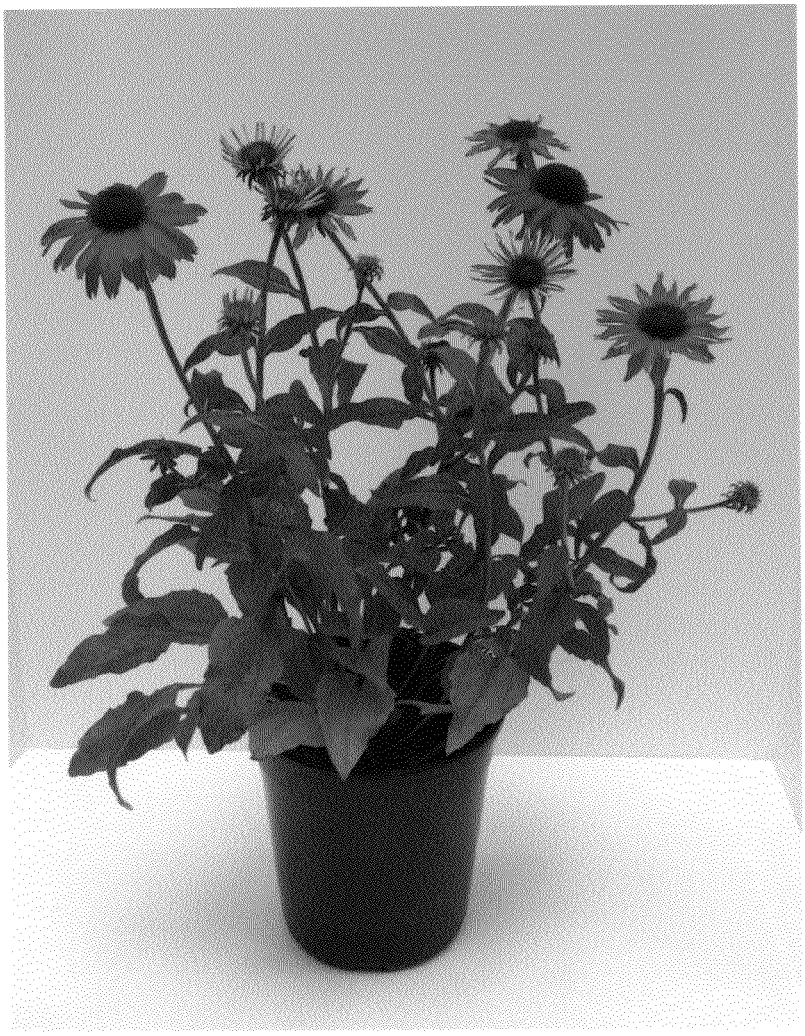
FIG. 1 illustrates a side view of the overall growth and flowering habit of 'Balsomsed'.
Figure 2:
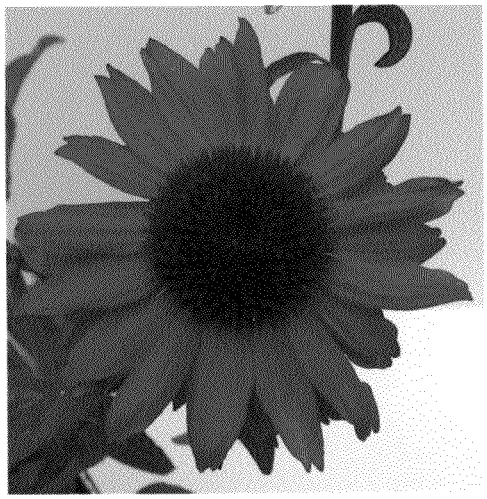
FIG. 2 illustrates a close-up view of an individual inflorescence of 'Balsomsed'.

The new cultivar has not been observed under all possible environmental conditions to date. Accordingly, it is possible that the phenotype may vary somewhat with variations in the environment, such as temperature, light intensity, and day length, without, however, any variance in genotype.

The chart used in the identification of colors described herein is The R.H.S. Colour Chart of The Royal Horticultural Society, London, England, 2007 edition, except where general color terms of ordinary significance are used. The color values were determined in June 2011 under natural light conditions in West Chicago, Ill.

The following descriptions and measurements describe plants produced from in vitro plantlets and grown in a glass-covered greenhouse under conditions comparable to those used in commercial practice. The plants were grown in Elburn, Ill. in 1-gallon pots for 16 weeks utilizing a soilless growth medium. Greenhouse temperatures were maintained at approximately 45° F. to 65° F. (7.2° C. to 18.3° C.) during the day and approximately 35° F. to 45° F. (1.7° C. to 7.2° C.) during the night. No supplemental lighting was provided. Measurements and numerical values represent averages of typical plants.

Botanical classification: *Echinacea×hybrida* cultivar Balsomsed.

Parentage:

*Female parent*.—Proprietary *Echinacea×hybrida* breeding selection designated 'E33-5', U.S. Pat. No. 7,982,110.

*Male parent*.—Bulk pollen mix of seven proprietary *Echinacea×hybrida* breeding selections designated 'E33-1' through 'E33-7', U.S. Pat. No. 7,982,110.

Propagation:

*Type*.—In vitro propagation is preferred, divisions are possible.

*Time to initiate roots in vitro*.—Approximately 30 days at 18° C.

*Time to produce a rooted plantlet in summer*.—Approximately 30 days at 18° C.

*Root description*.—Fine, fibrous; grey to light brown in color.

*Rooting habit*.—Moderate density, moderate branching.

Plant description:

*Commercial crop time*.—Approximately 16 weeks from a rooted tissue culture plantlet to finish in a 1 gallon container.

*Growth habit and general appearance*.—Compact-upright, narrow inverted triangle, herbaceous perennial.

*Growth rate*.—Moderately vigorous.

*Outdoor plant performance*.—Use as bedding plants or in mixed-container plantings; at least tolerant to temperatures up to 35° C. and hardy to USDA zone 4.

*Size*.—Height from soil level to top of plant plane: Approximately 41.8 cm. Width: Approximately 36.7 cm.

*Branching habit*.—No lateral branching, flowering stems grow from base. Quantity of main stems per plant: Approximately 5.

*Stems*.—Strength: Very strong. Aspect: Nearly erect. Shape: Rounded. Length to base of inflorescence: Approximately 23.0 cm. Diameter: Approximately 5.0 mm. Length of central internode: Approximately 3.3 cm. Texture: Densely pubescent with short strigose hairs. Color of young and mature stems: 144A.

Foliage description:

*General description*.—Form: Simple. Arrangement: Alternate.

*Leaves*.—Aspect: Perpendicular to stem, subtending with age. Shape: Narrowly ovate to lanceolate. Margin: Entire, widely serrate. Apex: Acute. Base: Attenuate. Venation pattern: Pinnate. Length of mature leaf: Approximately 9.5 cm. Width of mature leaf: Approximately 3.8 cm. Texture of upper surface: Slightly glossy, moderately pubescent with short strigose hairs. Texture of lower surface: Moderately pubescent with short strigose hairs. Color of upper surface of young foliage: Closest 137A with venation of 147C. Color of lower surface of young foliage: 137B to 137C with venation of 147C. Color of upper surface of mature foliage: Darker than 137A with venation of 147C. Color of lower surface of mature foliage: Closest to 138A with venation of 147C.

*Petiole*.—Shape: V-shaped. Length: Approximately 6.7 cm. Diameter: Approximately 3.0 mm. Texture of upper surface: Glabrous. Texture of lower surface: Glossy, sparsely covered with very short strigose hairs. Color of upper and lower surfaces: 147C.

Flowering description:

*Flowering habit*.—'Balsomsed' is freely flowering under outdoor growing conditions blooming from spring through autumn and with limited flowering under short winter days in a greenhouse environment.

*Lastingness of individual inflorescence on the plant*.—Approximately 3 weeks.

Inflorescence description:

*General description*.—Type: Solitary, composite. Persistent. Shape: Conical. Aspect: Facing upward. Arrangement: Terminal, held upright on strong peduncles. Fragrance: Faintly sweet. Quantity per plant: Approximately 8. Height: Approximately 3.8 cm. Diameter: Approximately 7.5 cm.

*Peduncle*.—Strength: Strong. Aspect: Erect to approximately 45° from vertical. Length: Approximately 15.5 cm. Diameter: Approximately 4.0 mm. Texture: Moderately pubescent with short strigose hairs. Color: 144A, with streaks of N186C.

*Bud*.—Quantity per plant: Approximately 2. Shape: Flattened globular with immature ray florets nearly erect. Length: Approximately 2.0 cm. Diameter: Approximately 2.5 cm. Color: Outer ray florets of 145C flushed with 44D and with a bud center of 143A.

*Ray florets*.—Quantity per inflorescence: Approximately 25. Arrangement: Slightly imbricate in a single whorl. Aspect: Perpendicular to disc, subtending with age. Shape: Narrowly elliptic to narrowly obovate. Appearance: Dull. Margin: Entire. Apex: Three acute tips. Base: Attenuate. Length: Approximately 3.6 cm. Width: Approximately 1.2 cm. Texture of upper and lower surfaces: Smooth, ribbed longitudinally. Color of upper surface when first open: 45A. Color of lower surface when first open: 36C with an overlay of 60C and 145C near apex. Color of upper surface when fully open: 45B. Color of lower surface when fully open: 36C with an overlay of 60D and 145C near apex.

*Disc florets*.—Disc diameter: Approximately 3.5 cm. Quantity per inflorescence: Approximately 300. Arrangement: Spirally arranged in center of inflorescence. Shape: Tubular. Margin of free portion: Entire. Apex: Five acute tips. Base: Fused into a tube. Length: Approximately 1.0 cm. Diameter: Approximately 2.0 mm. Texture: Glabrous. Color of upper or inner surface when first and fully open: 144B with tips of 187C. Color of lower or outer surface when first and fully open: 144A to 144B with tips of 187C and base of 145D.

*Receptacle*.—Shape: Conical. Height: Approximately 1.5 cm. Diameter: Approximately 1.4 cm. Color: 155D.

*Phyllaries*.—Quantity per inflorescence Approximately 65. Arrangement: In three whorls. Appearance: Dull, stiff. Shape: Narrowly ovate to lanceolate, strongly curved towards the peduncle. Margin: Entire. Apex: Acute. Base: Truncate. Length: Approximately 9.0 mm. Width: Approximately 3.0 mm. Texture of upper or inner surface: Glabrous. Texture of lower or outer surface: Glabrous with margins moderately to densely pubescent with short strigose hairs. Color of upper surface: 137A. Color of lower surface: 137B.

*Receptacle spines*.—Number of spines per disc: Approximately 300. Shape: Acicular. Length: Approximately 1.1 cm. Width at widest point: Approximately 2.0 mm. Apex: Acute. Base: Attenuate. Texture: Glabrous. Color: Apex of 187B transitioning through 163A to a mid-section of 144A and base of 145D.

*Reproductive organs*.—Androecium: Present on disc florets only. Stamen quantity: 5 per floret. Anther shape: Oblong, basifixed. Anther length: Approximately 3.0 mm. Anther color: Blackened 200A. Filament length: Approximately 2.0 mm. Filament color: 145D. Pollen amount: Moderate to abundant. Pollen color: 12A. Gynoecium: Present on disc florets only. Pistil quantity: 1 per floret. Pistil length: Approximately 1.0 cm. Stigma shape: Decurrent. Stigma color: 187C. Style length: Approximately 5.0 mm. Style color: 145C. Ovary color: 145D.

Seed and fruit production: Neither seed nor fruit production has been observed.

Disease and pest resistance: No particular resistance or susceptibility to other diseases or insects noted to date.

What is claimed is:

1. A new and distinct cultivar of *Echinacea* plant named 'Balsomsed', substantially as herein shown and described.

* * * * *